United States Patent
Marchais et al.

(10) Patent No.: US 11,782,045 B2
(45) Date of Patent: Oct. 10, 2023

(54) METHOD FOR ASSESSING THE CONCENTRATION OF URANIUM IN A SAMPLE BY GAMMA SPECTROMETRY, AND ASSOCIATED DEVICE

(71) Applicants: Orano Mining, Chatillon (FR); Commissariat à l'énergie atomique et aux énergies alternatives, Paris (FR)

(72) Inventors: Thomas Marchais, Saint-Paul-Lez-Durance (FR); Bertrand Perot, Venelles (FR); Cédric Carasco, St Julien (FR); Jean-Luc Ma, Manosque (FR); Hervé Toubon, Les Essarts-le-Roi (FR); Romain Goupillou, Limoges (FR)

(73) Assignees: ORANO MINING, Chatillon (FR); COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 328 days.

(21) Appl. No.: 17/294,058

(22) PCT Filed: Nov. 13, 2019

(86) PCT No.: PCT/EP2019/081147
§ 371 (c)(1),
(2) Date: May 14, 2021

(87) PCT Pub. No.: WO2020/099472
PCT Pub. Date: May 22, 2020

(65) Prior Publication Data
US 2022/0011287 A1   Jan. 13, 2022

(30) Foreign Application Priority Data
Nov. 14, 2018 (FR) ..................... 18 60485

(51) Int. Cl.
*G01N 33/24* (2006.01)
*G01N 23/083* (2018.01)
*G01T 1/36* (2006.01)

(52) U.S. Cl.
CPC .......... *G01N 33/24* (2013.01); *G01N 23/083* (2013.01); *G01T 1/362* (2013.01); *G01N 2223/616* (2013.01); *G01N 2223/626* (2013.01)

(58) Field of Classification Search
CPC ................ G01N 33/24; G01N 23/083; G01N 2223/616; G01N 2223/626; G01T 1/362
See application file for complete search history.

(56) References Cited

PUBLICATIONS

J.M. Domingos, A.A. Melo: "Determination of uranium and thorium ores using gamma spectrometry", Nuclear Instrumetns and Methods, vol. 48, 1967, pp. 28-32, XP001440408 DOI:10.1016/0029-554X(67)90457-0 (Year: 1967).*

(Continued)

*Primary Examiner* — Michael J Dalbo
*Assistant Examiner* — Kaleria Knox
(74) *Attorney, Agent, or Firm* — Davidson, Davidson & Kappel, LLC (57) ABSTRACT

A method for assessing the mass concentration of uranium in a sample of uranium-bearing material by gamma spectrometry, includes a) acquiring (200) an energy spectrum of gamma radiation from the sample using a scintillator detector, the energy spectrum (100) comprising at least a first energy band (110) between 87 keV and 110 keV, and a second energy band (120) between 560 keV and 660 keV, the second energy band comprising at least one energy line (130) at 609 keV from $^{214}$Bi, b) calculating (210) an initial mass concentration of uranium ($Cm_{U0}$) using the energy spectrum, c) measuring (220) a parameter representative of the height of the sample and a parameter representative of the density of the sample, d) calculating (230) a corrective (Continued)

coefficient (K), and e) calculating (240) a corrected mass concentration of uranium ($Cm_U$) using the initial mass concentration of uranium ($Cm_{U0}$) and the corrective coefficient (K).

10 Claims, 4 Drawing Sheets

(56) References Cited

PUBLICATIONS

T.Marchais et al., "Gamma-ray spectroscopy measurements and simulations for uranium mining", EPJ Web of Conferences, vol. 170, 10 jamvier 2018 (Jan. 1, 2018), pp. 05003, XP055526215 (Year: 2018).*
Enghauser "Uranium gamma spectroscopy training" NISA, pp. 1-35 (Year: 2018).*
Corresponding Search Report for PCT/EP2019/081147.
Corresponding Search Report for FR1860485.
J.M. Domingos, A.A. Melo: "Determination of Uranium and Thorium Ores Using Gamma Spectrometry", Nuclear Instruments and Methods, vol. 48, 1967, pp. 28-32.
T.Marchais et al: "Gamma Ray Spectroscopy Measurements and Simulations for Uranium Mining" EPJ Web of Conferences, vol. 170, Jan. 10, 2018.

* cited by examiner

METHOD FOR ASSESSING THE CONCENTRATION OF URANIUM IN A SAMPLE BY GAMMA SPECTROMETRY, AND ASSOCIATED DEVICE

The present disclosure relates to a method for assessing the mass concentration of uranium in a sample of ore by gamma spectrometry.

BACKGROUND

Uranium occurs naturally in the form of three isotopes: $^{238}$U, $^{235}$U and $^{234}$U, the latter being derived from the decay chain of $^{238}$U. $^{238}$U is overwhelmingly predominant and represents more than 99.2% of total uranium.

The isotopes $^{238}$U and $^{235}$U successively decay into different chemical elements known as daughter nuclides until the chemical element obtained becomes stable. Each decay is accompanied most often by the emission of high-energy photons also known as X rays or gamma rays, the energy spectrum of which is typically comprised between a few tens of keV and more than 2000 keV. The unit of measurement for radiation is expressed in (number of decays) counts per unit of time, for example in counts per second.

It is possible to use the abovementioned type of method in mining exploration and exploitation in order to characterise the uranium content of rock samples. In the case of mining prospecting, these measurements are carried out in-situ or on the rock samples, for example obtained from boreholes. These measurements typically make it possible to characterise the uranium potential of a region. In mining development-operation, the method may for example be used at the plant in order to perform a sorting of the ore on the basis of its uranium content and thus adapt the processing treatment of the ore accordingly.

The standards NF M60-790-3 and NF ISO 18589-3 describe, for example, a measurement by high resolution gamma spectrometry based on the detection of the 1001 keV energy line of $^{234m}$Pa (protactinium-234m), a descendant (intermediate decay product) of the uranium series or chain. However, the low intensity of this line leads to long measurement times, up to several hours for samples having low mass (ie a few hundred grammes) or low uranium content (less than 1000 ppm$_U$). The selection of this line rather than the higher intensity lines of $^{214}$Pb (lead-214) or $^{214}$Bi (bismuth-214), descendants of $^{238}$U situated at the back-end of the radioactive chain, derives from the risk of disequilibrium in the decay chain of $^{238}$U. In case of disequilibrium, a measurement of the uranium content based on the gamma radiation of a daughter element situated at the back-end of the decay chain leads to an erroneous, overestimated or underestimated value depending on the type of disequilibrium (activity ratio of radioelements at the start and end of the chain less than or greater than 1.00, respectively), of the actual uranium content. This disequilibrium is generally observed for low uranium content deposits subject to the phenomena of differential leaching (eg uranium deposits of such type as "roll fronts") which constitute a large part of the uranium deposits exploited in the world.

In order to overcome this drawback, other energy lines may be used, such as the 92 keV energy line of $^{234}$Th or the 98 keV X-ray fluorescence line. This makes it possible to significantly reduce the counting times. The Applicants have filed a patent application FR 1851744 relating to a mass concentration determination method for determining the mass concentration of uranium in a sample of uranium ore using both the 92 keV energy line and the 98 keV energy line, which uses an expensive germanium detector and requires cooling of the crystal.

Domingos and Melo (1967) in "*Determination of uranium and thorium ores using gamma spectrometry*", *Nuclear Instruments and Methods* 48, 28-32, propose using a sodium iodide (NaI) detector in low resolution spectrometry, which provides the ability to reduce the costs generated by these measurements. The method described is based on a spectral decomposition into three distinct energy zones or bands:

from 52 keV to 108 keV, to measure the contribution of uranium in the spectra thanks to the gamma emissions at 63 keV and 92 keV of $^{234}$Th. This zone is also potentially impacted by the $^{232}$Th with the emission of numerous X rays and of an 84 keV gamma ray of $^{228}$Th in its radioactive decay chain;

from 560 to 660 keV, to measure the chain-end contribution of uranium. This zone is dominated by the gamma emission of $^{214}$Bi at 609 keV;

from 2.46 to 2.76 MeV, in order to take into account in a very selective manner the $^{232}$Th thanks to the emission of a gamma radiation of $^{208}$Tl at 2614 keV (free of interference by other radiations at this energy).

Each zone or band corresponds to a count rate which is assumed to be a linear combination of the uranium and thorium content of the sample, and of the disequilibrium factor of the radioactive decay chain between uranium and radium.

By using reference samples for which the uranium content, thorium content and disequilibrium are known, it is possible, for example by means of the method of least squares, to determine the coefficients of each of the linear combinations and thus to obtain the empirical relationships for uranium and thorium content.

However, this method has a major drawback. In order to obtain reliable estimates of the uranium content, the samples to be analysed must all exhibit physical characteristics that are similar to the reference samples.

SUMMARY

An object of the present disclosure is to provide a mass concentration assessment method for faster and more precise assessment of the mass concentration of uranium of an ore sample, in particular for samples that have variable characteristics in terms of uranium content, radioactive disequilibrium, mineralogy, geometry (filling height of the container) and density.

To this end, a method of the aforementioned type is provided, the sample of uranium-bearing material having a density and a height, the method comprising the following steps:

acquiring an energy spectrum of gamma radiation from the sample using a scintillator detector, the energy spectrum comprising at least a first energy band between 87 keV and 110 keV, and a second energy band between 560 keV and 660 keV, the second energy band comprising at least one 609 keV energy line of $^{214}$Bi;

calculating an initial mass concentration of uranium using the area of the first energy band, the area of the second energy band, and the net area of the 609 keV energy line of $^{214}$Bi;

measuring a parameter that is representative of the height of the sample and a parameter that is representative of the density of the sample;

calculating a corrective coefficient using the parameter that is representative of the height of the sample, the parameter that is representative of the density of the sample, and the initial mass concentration of uranium;

calculating a corrected mass concentration of uranium using the initial mass concentration of uranium and the corrective coefficient.

Thus, the method according to the present disclosure provides the ability to determine the mass concentration of uranium in a sample of a uranium-bearing material taking into account its physical characteristics, and thus to obtain more precise concentration values. The use of the first energy band between 87 keV and 110 keV is particularly stable with respect to heterogeneities and self-attenuation with a high uranium content compared to the 53 keV-108 keV band used in the method of Domingos and Melo (1967), the increased attenuation of the 92 keV gamma ray of $^{234}$Th in such cases being in fact counterbalanced by the increase in the X-ray fluorescence of uranium and consequently of the 98 keV X ray. It is also more stable with respect to other causes of uncertainties such as lack of knowledge of the precise mineralogy of the uranium-bearing material, given that it does not incorporate the gamma emission at 63 keV of $^{234}$Th of which the self-absorption is very sensitive to this parameter.

The method according to the present disclosure provides the means for a rapid assessment of the mass concentration of uranium in the sample of uranium-bearing material. The measurements are inexpensive because the method does not require a hyper-pure germanium semiconductor detector, a "simple" sodium iodide scintillation detector makes it possible to obtain reliable and precise measurements.

According to particular embodiments, the method according to the present disclosure comprises one or more of the following characteristic features, taken into consideration in isolation or in accordance with all the possible technical combinations:

the initial mass concentration of uranium is calculated using a ratio between the area of the first energy band and the area of the second energy band;

the sample has a U/Rn radioactive disequilibrium, the initial mass concentration of uranium being calculated using a parameter that is representative of the U/Rn radioactive disequilibrium;

the initial mass concentration of uranium is in addition calculated using at least two calibration coefficients;

the calibration coefficients are determined experimentally using a plurality of standard samples or by numerical simulation.

the initial mass concentration of uranium is calculated using two calibration coefficients and a ratio $$\frac{\frac{C_u}{C_{Rn}} - \beta}{\alpha},$$

the said ratio being representative of a U/Rn radioactive disequilibrium of the sample;

the initial mass concentration of uranium is calculated using the following equation:

$$Cm_{u0} = \frac{r_{U/U(238)} \times 10^6 \times M(_{92}^{238}U) \times T_{\frac{1}{2}}(_{92}^{238}U)}{\ln(2) \times N_A \times M_{ech}} \times$$

$$\frac{S_n(609 \text{ keV})}{E\!f\!f_{609 \text{ keV}} \times I_{609 \text{ keV}}(_{83}^{214}Bi) \times T_C} \times \frac{\frac{C_U}{C_{Rn}} - \beta}{\alpha}$$

where:

$r_{U/U\ (238)}$: the mass ratio ($^{235}$U+$^{238}$U)/$^{238}$U in natural uranium equal to 1.0072;

$N_A$: the Avogadro constant;

$M(_{92}^{238}U)$: the molar mass of $^{238}$U;

$T_{\frac{1}{2}}(_{92}^{238}U)$ the half-life of $^{238}$U;

ln: the natural logarithm;

$M_{ech}$: the mass of the sample;

$S_n$(609 keV): the net area in the 609 keV line;

$E\!f\!f_{609\ keV}$: the efficiency of the scintillator detector (14) at 609 keV;

$I_{609\ keV}(_{214}^{83}Bi)$: the emission intensity of $^{214}$Bi at 609 keV;

$T_C$: the counting "live time" corrected for the dead time of the scintillator detector.

the corrected mass concentration of uranium is calculated by multiplying the initial mass concentration of uranium and the corrective coefficient;

the corrective coefficient is calculated using an equation of the following form:

$K(d,h,Cm_{U0})=a_0+a_1 \times Cm_{U0}+a_2 \times d+a_3 \times h+a_4 \times d \times h+a_5 \times d \times h \times Cm_{U0}+a_6 \times Cm_{U0}^3+a_7 h^3$ where d is the parameter that is representative of the density, h the parameter that is representative of the height, and $a_0$ to $a_7$ are the coefficients.

The present disclosure also relates to a mass concentration assessment device for assessing the mass concentration of uranium in a sample of a uranium-bearing material, the sample having a density and a height, the device comprising:

an acquisition module for acquiring an energy spectrum of gamma radiation of the sample by means of a detector, the energy spectrum comprising at least a first energy band between 87 keV and 110 keV, and a second energy band between 560 keV and 660 keV, the second energy band comprising a 609 keV energy line of $^{214}$Bi;

a calculation module for calculating an initial mass concentration of uranium by using the area of the first energy band, the area of the second energy band, and the net area of the 609 keV energy line of $^{214}$Bi;

a measurement module for obtaining a measurement of a parameter that is representative of the height of the sample and of a parameter that is representative of the density of the sample;

a calculation module for calculating a corrective coefficient, by using a parameter that is representative of the height of the sample, a parameter that is representative of the density of the sample, and the initial mass concentration of uranium calculated by the calculation module;

a calculation module for calculating a corrected mass concentration of uranium that is corrected by using the initial mass concentration of uranium and the corrective coefficient, each respectively calculated by the corresponding calculation module and the calculation module.

BRIEF SUMMARY OF THE DRAWINGS

The present disclosure will be better understood upon reading the description that follows, provided solely by way of example, and made with reference to the drawings in which.

DETAILED DESCRIPTION

In the remainder of the description, the terms "mass concentration" and "content" are considered to be synonymous. The terms "line", "energy line", "peak" or "energy peak" are also considered to be synonymous.

Figure 1:
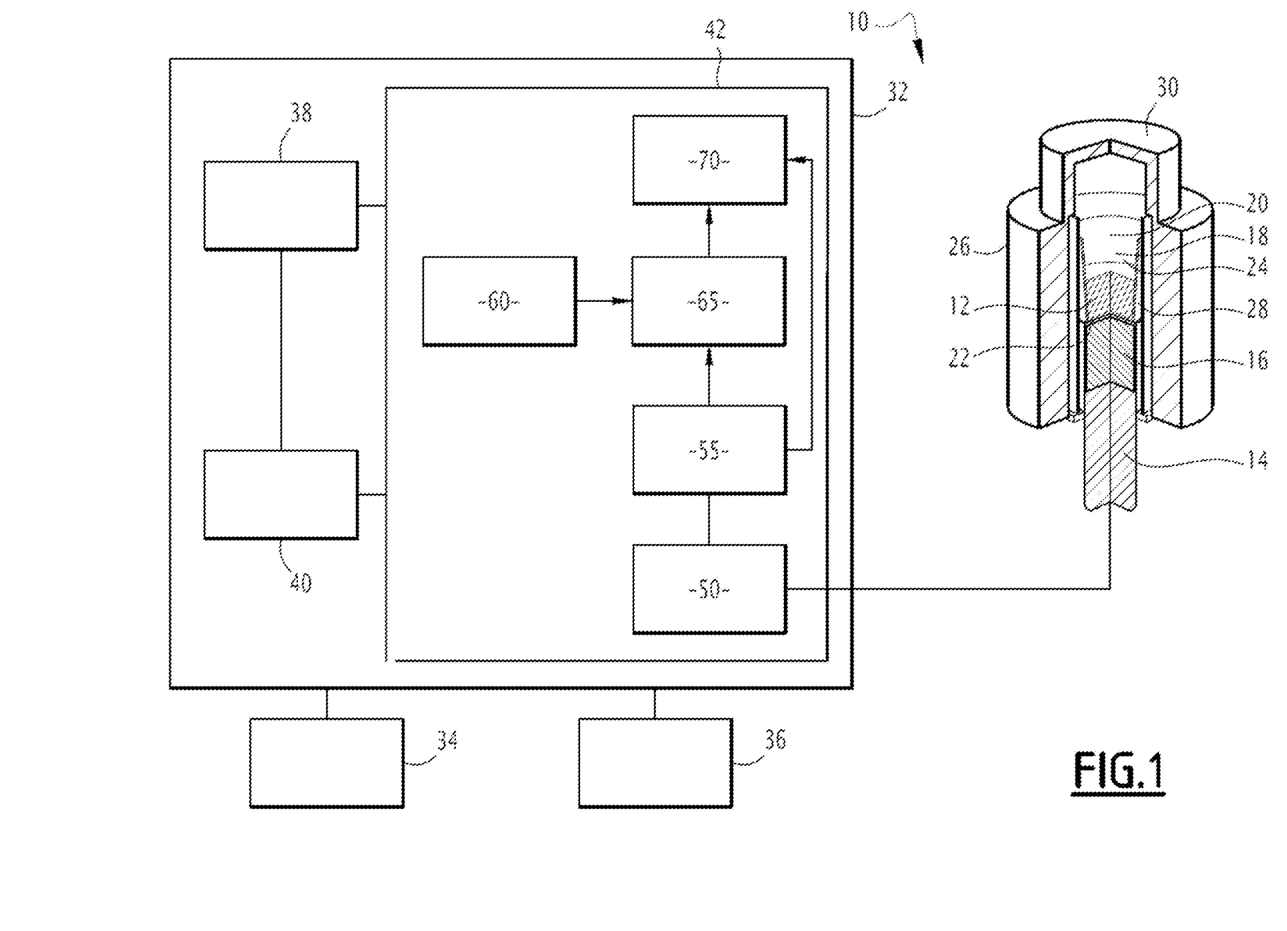
FIG. 1 is a schematic representation of a mass concentration assessment device for assessing the mass concentration of uranium in an ore sample according to the present disclosure.

A mass concentration assessment device 10 for assessing the mass concentration of uranium in a sample 12 of a uranium-bearing material is shown schematically in FIG. 1.

The device 10 comprises a scintillator detector 14. The scintillator detector 14 comprises for example a crystal 16 of sodium iodide (NaI).

The crystal 16 is for example a 3"×3" crystal, that is to say that the crystal 16 has a diameter of 3" and a length of 3".

The sample 12 of uranium-bearing material is for example obtained from a drill core or crushed ore that is derived from the exploration or operation of a mine. The sample of uranium-bearing material is placed in a container 18 providing a bed of material of height h. The container 18 is for example made of PVC.

Figure 2:
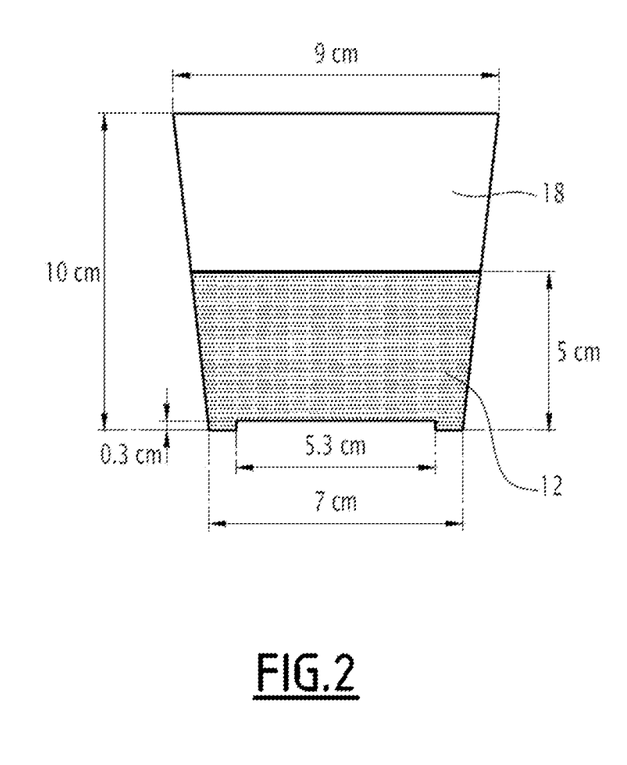
FIG. 2 is a schematic representation of a sample used in the device shown in FIG. 1.

FIG. 2 shows the geometry of the container 18 and of the sample 12.

The container 18, in this instance having frustoconical shaped form, comprises a lateral wall 20 and a bottom 22 that defines a receiving volume 24 for receiving the crushed sample 12.

The wall 20 of the container 18 is for example one millimetre thick.

As shown in FIG. 1, the bottom 22 of the container 18 is intended to be brought into contact with the scintillator detector 14 during the acquisition of the gamma energy spectrum.

The sample 12 is preferably finely crushed so as to obtain a grain size of less than one millimetre in order to limit the measurement uncertainties linked to the presence of heterogeneities.

The sample 12 is advantageously homogenised. The term "homogenised" is understood to indicate the absence of any particular graded bedding or granoclassification in the ore sample.

For example, the sample 12 is crushed by using a ring mill.

The uranium-bearing material is arranged inside the container 18 without compacting.

A standard sample is used as a reference sample in the method according to the present disclosure.

For example the standard sample has a bulk density (or apparent density) d=1.3 and the height of the bed of the standard sample is h=5 cm.

The term "bulk density" is understood to refer to the density of the sample without compacting.

The standard sample comprises silicon dioxide ($SiO_2$).

The uranium content of the standard sample is for example 1000 $ppm_U$, that is to say 1000 milligrammes of uranium per kilogramme of sample.

The device 10 further comprises a shielding enclosure 26, which is for example cylindrical with a circular base.

The shielding enclosure 26 defines a housing 28, which is for example cylindrical with a circular base, intended to receive the container 18 with the sample 12 and a part of the scintillator detector 14.

The shielding enclosure 26 is designed to cover the lateral wall 20 of the container 18 and part of the scintillator detector 14, in order to overcome the background noise coming from the measurement chamber.

The shielding enclosure 26 is preferably made of lead. The thickness of the enclosure 26 is for example 4.5 cm.

The shielding enclosure 26 is preferably lined with a layer of copper, for example measuring 3 mm, in order to absorb the lead fluorescence X-rays.

The shielding enclosure 26 is closed by a cap 30, preferably made of lead, arranged on an upper part of the shielding enclosure 26.

The device 10 includes a computing unit 32 for assessing the mass concentration of uranium in the sample 12, a display unit 34 connected to the computing unit 32 to display the results supplied by the computing unit 32 and a human-machine interface 36.

The computing unit 32 comprises a database 38.

The database 38 is intended to record the results supplied by the computing unit 32.

The computing unit 32 comprises a processor 40 and a memory storage unit 42 that receives software modules. The processor 40 is capable of executing the software modules received in the memory storage unit 42 and of operationally implementing the method according to the present disclosure.

The memory storage unit 42 comprises an acquisition module 50 for acquiring an energy spectrum of gamma radiation of the sample 12 by means of the scintillator detector 14.

Figure 3:
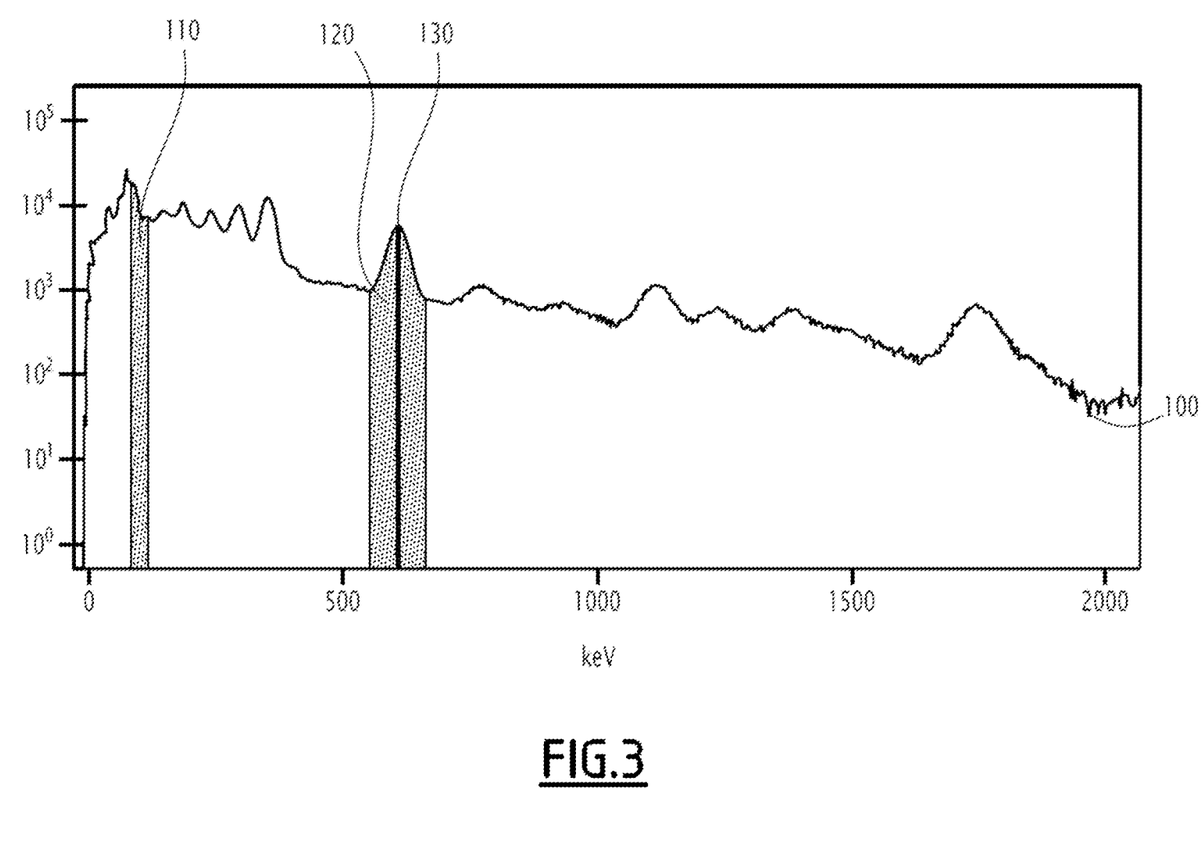
FIG. 3 is an example of the gamma energy spectrum acquired by the device shown in FIG. 1.

FIG. 3 shows an example of an energy spectrum 100 acquired by the acquisition module 50.

The energy spectrum 100 includes at least a first energy band 110 between 87 keV and 110 keV, and a second energy band 120 between 560 keV and 660 keV. The second energy band 120 comprises a 609 keV energy line 130 of $^{214}Bi$.

The memory storage unit 42 further comprises a calculation module 55 for calculating an initial mass concentration of uranium $Cm_{U0}$ by using the area $C_U$ of the first energy band 110, the area $C_{Rn}$ of the second energy band 120, and the net area of the 609 keV energy line 130 of $^{214}Bi$.

The net area at 609 keV derives solely from the gamma emission of $^{214}Bi$, after subtraction of the Compton scattering continuum, for example effected in an ad hoc manner by using a software application for processing energy spectra.

The areas of the first energy band 110 $C_U$ and of the second energy band 120 $C_{Rn}$ correspond to the raw areas without correction of the Compton scattering continuum.

The acquisition time depends on the U/Rn (Uranium/Radon) radioactive disequilibrium of the uranium-bearing material sample and on the average uranium content of the sample 12. It is typically between less than one minute and 25 minutes.

It is recalled that secular equilibrium is a situation in which the quantity (or activity) of a radioactive isotope remains constant because its production rate (due to decay of a parent isotope) is equal to its decay rate. Where such is not the case it is referred to as radioactive disequilibrium. This state of disequilibrium is observed in particular between $^{222}$Rn and uranium $^{238}$U due to the volatility of radon.

The memory storage unit 42 comprises a module 60 for obtaining a measurement of a parameter that is representative of the height "h" of the bed of the sample 12 and of a parameter that is representative of the density "d" of the sample 12.

The parameters representative of the height "h" of the bed of the sample 12 and of the density "d" of the sample 12 are for example measured manually by an operator and entered into the module 60 of the device 10.

The memory storage unit 42 comprises a calculation module 65 for calculating a corrective coefficient K, using the parameter that is representative of the height of the sample 12, the parameter that is representative of the density of the sample 12, and the initial mass concentration of uranium $Cm_{U0}$ calculated by the calculation module 50.

The memory storage unit 42 comprises a calculation module 70 for calculating a corrected mass concentration of uranium $Cm_U$ using the initial mass concentration of uranium $Cm_{U0}$ and the corrective coefficient K, each respectively calculated by the corresponding calculation module 55 and the calculation module 65.

The modules 50, 55, 60, 65 and 70 are programmed to implement the method according to the present disclosure, as described in the following sections.

Figure 4:
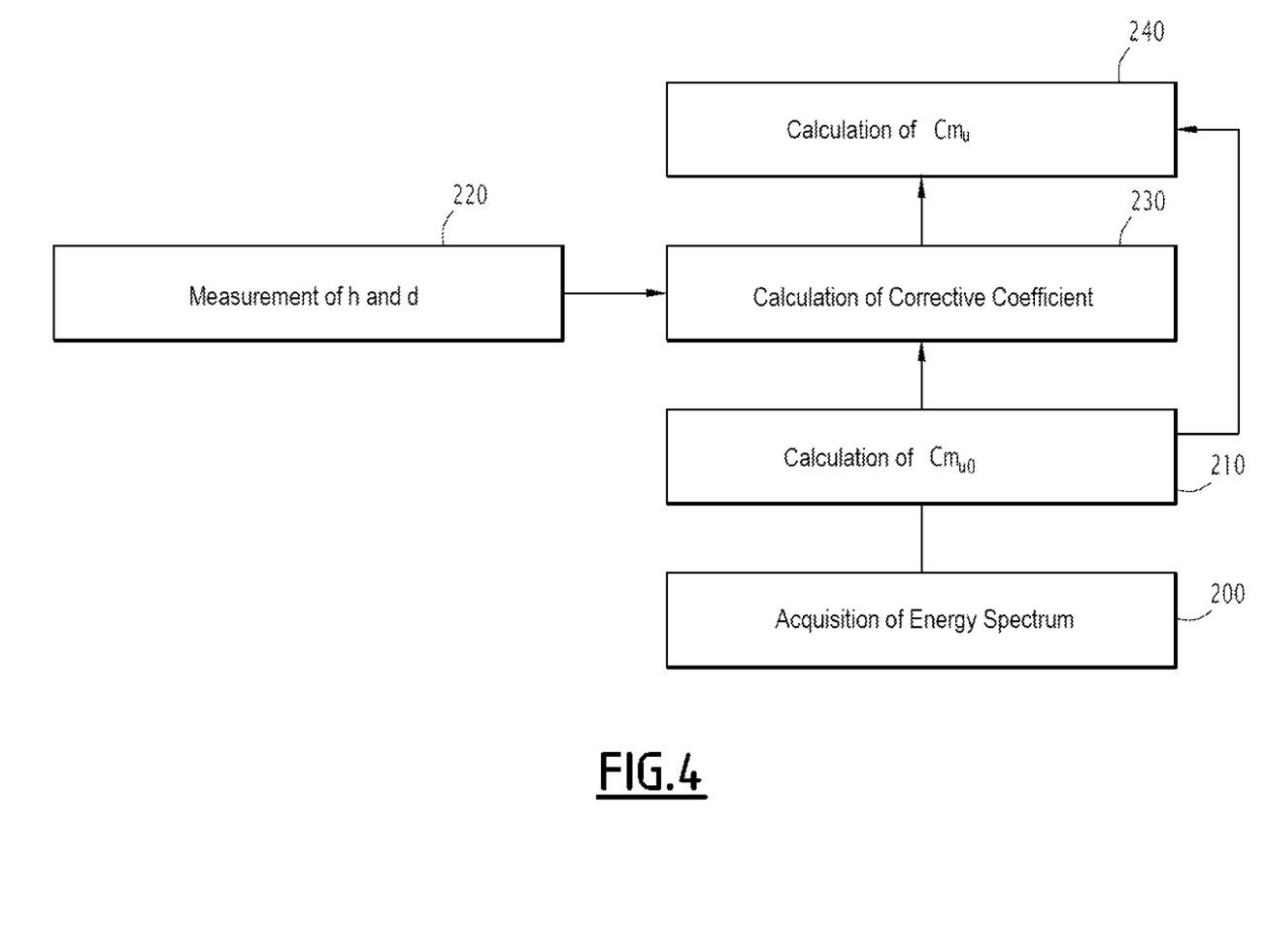
FIG. 4 is a schematic representation of a method according to the present disclosure.

FIG. 4 presents the steps of a mass concentration assessment method for assessing the mass concentration of uranium in a sample 12 according to the present disclosure.

The method comprises an acquisition step 200 for acquiring an energy spectrum 100 of gamma radiation from the sample 12 using a scintillator detector 14. The detector 14 is preferably of the type described above. As previously mentioned above, the scintillator detector 14 comprises, for example, a crystal 16 of sodium iodide (NaI).

The energy spectrum 100 comprises at least a first energy band 110 between 87 keV and 110 keV, and a second energy band 120 between 560 keV and 660 keV. The second energy band comprises at least one 609 keV energy line 130 of $^{214}$Bi (FIG. 3).

The method thus then includes a calculation step 210 for calculating an initial mass concentration of uranium $Cm_{U0}$ by using the area $C_U$ of the first energy band 110, the area $C_{Rn}$ of the second energy band 120, and the net area of the 609 keV energy line 130 of $^{214}$Bi.

The initial mass concentration of uranium $Cm_{U0}$ is calculated by using a ratio ($C_U/C_{Rn}$) between the area $C_U$ of the first energy band 110 and the area $C_{Rn}$ of the second energy band 120, which is a parameter that is representative of the U/Rn radioactive disequilibrium.

The initial mass concentration $Cm_{U0}$ of uranium is in addition calculated using two calibration coefficients β.

More particularly, the initial mass concentration of uranium $Cm_{U0}$, is calculated using the following equation:

$$Cm_{u0} = \frac{r_{U/U(238)} \times 10^6 \times M(^{238}_{92}U) \times T_{\frac{1}{2}}(^{238}_{92}U)}{\ln(2) \times N_A \times M_{ech}} \times \frac{S_n(609 \text{ keV})}{\text{Eff}_{609 \text{ keV}} \times I_{609 \text{ keV}}(^{214}_{83}Bi) \times T_C} \times \frac{\frac{C_U}{C_{Rn}} - \beta}{\alpha}$$

where:

$r_{U/U\ (238)}$: the mass ratio (U$^{235}$+U$^{238}$)/$^{238}$U in natural uranium which is equal to 1.0072;

$N_A$: Avogadro constant (6.022×10$^{23}$ mol$^{-1}$);

$M(_{92}^{238}U)$: the molar mass of $^{238}$U (238.0507 g·mol$^{-1}$);

$T_{1/2}(_{92}^{238}U)$: the half-life (radioactive period) of $^{238}$U (4.468×10$^9$ years);

ln: the natural logarithm;

$M_{ech}$: the mass of the sample (in grammes);

$S_n$ (609 keV): the net area in the 609 keV line (number of counts);

$\text{Eff}_{609\ keV}$: the efficiency of the detector at 609 keV (dimensionless);

$I_{609\ keV}$ ($_{83}^{214}$Bi): the emission intensity of $^{214}$Bi at 609 keV (number of photons emitted per decay) equal to 46.1% according to the database Evaluated Nuclear Structure Data File of the International Atomic Energy Agency—IAEA);

$T_C$: the counting "live time" (in seconds) corrected for the dead time of the detector 14.

The initial mass concentration of uranium $Cm_{U0}$ is expressed here in ppm$_U$, that is to say, in milligrammes of uranium per kilogramme of sample 12, hence the conversion factor 10$^6$ in the preceding equation.

The efficiency $\text{Eff}_{609\ keV}$ is calculated for example with the Monte-Carlo N-Particle code (MCNP) which provides the ability to model the transport of X and gamma rays emitted in the sample to the detector and then the interaction thereof (energy deposits) in the germanium crystal ("MCNP6TM, User's manual—Version 1.0—LA-CP-13-00634, Rev. 0, Denise B. Pelowitz". May-2013).

The calibration coefficients α, β are experimentally determined using a plurality of standard samples or by means of numerical simulation.

The calibration coefficients α, β are connected to the area $C_U$ of the first energy band and 110, to the area $C_{Rn}$ of the second energy band 120, to the U/Rn radioactive disequilibrium of the sample by the equation:

$$\frac{A(_{92}^{238}U)}{A(_{83}^{214}Bi)} = \frac{\frac{C_U}{C_{Rn}} - \beta}{\alpha}$$

Experimentally, the coefficients α, β are determined by having available a plurality of standard samples that exhibit different U/Rn disequilibriums. In this case, the standard samples exhibit physical characteristics (mineralogy, height, and density) and a uranium content that is substantially identical to those of the standard sample defined here above.

The term "substantially identical" is understood to indicate a bed height of 5 cm and a density of 1.3 with a precision of the order of % (a maximum of 3%), as well as identical mineralogy (uranium-bearing material with the same provenance), and a uranium content of 1000 ppm$_U$, with a tolerance of ±500 ppm$_U$.

It is to be noted that for the uranium content, the effect is not significant up to a few thousand ppm$_U$.

The measurement of the $C_U/C_{Rn}$ ratio as a function of the U/Rn disequilibrium of the various standard samples makes it possible to obtain the calibration coefficients α, β for example by linear regression.

The value of calibration coefficients α, β depends on the measurement geometry, the type of detector 14, and the characteristics of the sample 12 (height, density, and uranium content). In the event of a change of detector 12, or for another measurement geometry, it is then necessary for the calibration coefficients to be determined anew.

The method comprises a measurement step 220 of measuring a parameter that is representative of the height of the sample 12 and a parameter that is representative of the density of the sample 12.

According to one particular embodiment, the step 220 is carried out before the acquisition step 200 and/or the calculation step 210.

The height of the sample 12 is for example measured by using a graduated ruler or an optical method.

The density of the sample 12 is for example measured using any appropriate protocol known to the person skilled in the art. For example, the mass $M_{ech}$ of the sample 12 is measured with a balance and the volume $V_{ech}$ of the sample 12 is determined by immersing it in water in a graduated cylinder. The M/V ratio is used to obtain the density.

The method then comprises a calculation step 230 of calculating a corrective coefficient K, using the parameter that is representative of the height of the sample 12, the parameter that is representative of the density of the sample 12, and the initial mass concentration of uranium $Cm_{U0}$.

The corrective coefficient K makes it possible to take into account the variation in the density of the sample 12, the height of the sample 12, and the uranium content $Cm_{U0}$ of the sample 12, and is a function of these physical parameters.

The value of the corrective coefficient is preferably obtained by carrying out a multiparametric study by numerical simulation.

For example, the spectral response of more than 800 configurations of samples that exhibit filling heights h varying from 1 to 9 cm, densities d varying from 1 to 1.6, and uranium contents $Cm_{U0}$ comprised between 100 $ppm_U$ and 100,000 $ppm_U$ is simulated.

It is thus then possible to calculate a corrective factor $K(d, h, Cm_{U0})$ that may be used to correct the variations induced by the height of the sample, the density and the uranium content, on the calibration coefficients α, β calculated for the standard sample, using an equation of the following form:

$$K(d,h,Cm_{U0})=a_0+a_1 \times Cm_{U0}+a_2 \times d+a_3 \times h+a_4 \times d \times h+a_5 \times d \times h \times Cm_{U0}+a_6 \times Cm_{U0}^3+a_7 \times h^3$$

The coefficients $a_0$ to $a_7$ are determined by multilinear regression.

The method according to the present disclosure finally comprises a calculation step 240 of calculating a corrected mass concentration of uranium $Cm_U$ using the initial mass concentration of uranium $Cm_{U0}$ and the corrective coefficient K.

More particularly, the corrected mass concentration of uranium $Cm_U$ is obtained by the product of the initial mass concentration of uranium $Cm_{U0}$ and the corrective coefficient K:

$$Cm_U = Cm_{U0} \times K$$

The inventors have carried out a study on the uncertainty associated with the value of the corrected uranium mass concentration $Cm_U$ assuming a sample 12 that is finely crushed (grain less than 2 mm), and homogenised, with a U/Rn disequilibrium greater than 0.1, and a counting time that is long enough to obtain a statistical uncertainty of less than 1% on the ratio of counts $C_U/C_{Rn}$.

This assumption is borne out when the acquisition time is greater than a minimum value $T_{min}$ which is equal to:

$$T_{min} = \frac{\left(\frac{1}{\tau_U}\right)+\left(\frac{1}{\tau_{Rn}}\right)}{(1\%)^2}$$

Where:

$\tau_U$: the count rate in the first energy band 110, measurable starting from the initial minutes of acquisition and which, after any duration T, is equal to $$\tau_U(T) = \frac{C_U(T)}{T};$$

$\tau_{Rn}$: the count rate in the second energy band 120, which is equal to $$\tau_{Rn}(T) = \frac{C_{Rn}(T)}{T};$$

these count rates remain constant with the exception of statistical counting fluctuations and they hardly vary anymore when $T_{min}$ is reached.

The calculation of the uncertainty on the uranium content takes into account separately the uncertainty due to the characteristics of the sample 12, the uncertainty due to the mineralogy of the sample 12, the uncertainty due to a possible heterogeneity of the sample 12, the uncertainty due to the counting statistics, and finally the uncertainty due to the measurement of the specific activity of $^{214}$Bi.

The uncertainty associated with the value of the corrected uranium mass concentration $Cm_U$, obtained by quadratic sum of the various uncertainties mentioned above, is 20% if the sample 12 is finely crushed (2 mm) and homogenised. For a more coarsely crushed sample 12 (8 mm), this uncertainty amounts to approximately 30%.

An experimental validation was also performed using 38 samples 12 having a uranium content of between 100 and 100,000 $ppm_U$. For each content level, different U/Rn disequilibria were selected.

For each sample 12, a reference uranium content was measured by inductively coupled plasma mass spectrometry (ICP-MS) with a level of precision of the order of 10%.

The method according to the present disclosure and the method described in Domingos and Melo (1967) mentioned above were applied to the 38 samples.

The mean relative deviation from the reference content is about 33% using an energy band ranging from 52 keV to 108 keV in order to measure the contribution of uranium in the spectrum, as in the method of Domingos and Melo (1967).

The mean relative deviation from the reference content is of the order of 15% using the method according to the present disclosure with an energy band between 87 keV and 110 keV.

Thus, by advantageously taking into account the corrective factor K, the method according to the present disclosure makes it possible to obtain a value of the mass concentration of uranium that is more precise than the methods of the state of the art. The use of the first energy band between 87 keV and 110 keV is in effect particularly stable with respect to heterogeneities and self-attenuation as compared to the 53 keV-108 keV band used by the method of Domingos and Melo (1967), but it is also less sensitive to variations in the mineralogy of the ore.

The method according to the present disclosure serves to enable a rapid assessment of the mass concentration of uranium of the sample. The measurements are inexpensive because the method does not require a germanium semiconductor detector. A "simple" sodium iodide scintillation detector provides the ability to obtain reliable and precise measurements.

What is claimed is:

1. A method for assessing a concentration of uranium in a sample of uranium-bearing material by gamma spectrometry, the sample having a density and a height, the method comprising:
   acquiring an energy spectrum of gamma radiation from the sample using a scintillator detector, the energy spectrum comprising at least a first energy band between 87 keV and 110 keV, and a second energy band between 560 keV and 660 keV, the second energy band comprising at least one energy line at 609 keV of $^{214}$Bi;
   calculating an initial mass concentration of uranium using an area of the first energy band, an area of the second energy band, and a net area of the 609 keV energy line of $^{214}$Bi;
   measuring a parameter that is representative of the height of the sample and a parameter that is representative of the density of the sample;
   calculating a corrective coefficient using the parameter that is representative of the height of the sample, the parameter that is representative of the density of the sample, and the initial mass concentration of uranium; and
   calculating a corrected mass concentration of uranium using the initial mass concentration of uranium and the corrective coefficient.

2. The method according to claim 1, wherein the initial mass concentration of uranium is calculated using a ratio between the area of the first energy band and the area of the second energy band.

3. The method according to claim 1, wherein the sample has a U/Rn radioactive disequilibrium, the initial mass concentration of uranium being calculated using a parameter that is representative of the U/Rn radioactive disequilibrium.

4. The method according to claim 1, wherein the initial mass concentration of uranium is in addition calculated using at least two calibration coefficients.

5. The method according to claim 4, wherein the at least two calibration coefficients are determined experimentally using a plurality of standard samples or by numerical simulation.

6. The method according to claim 4, wherein the initial mass concentration of uranium is calculated using two calibration coefficients and a ratio, said ratio being representative of a U/Rn radioactive disequilibrium of the sample.

7. The method according to claim 6, wherein the initial mass concentration of uranium $Cm_{U0}$ is calculated using the following equation:

$$Cm_{u0} = \frac{r_{U/U(238)} \times 10^6 \times M(_{92}^{238}U) \times T_{\frac{1}{2}}(_{92}^{238}U)}{\ln(2) \times N_A \times M_{ech}} \times$$

$$\frac{S_n(609 \text{ keV})}{\text{Eff}_{609 \text{ keV}} \times I_{609 \text{ keV}}(_{83}^{214}Bi) \times T_C} \times \frac{\frac{C_U}{C_{Rn}} - \beta}{\alpha}$$

where:
   $r_{U/U(238)}$: a mass ratio $(^{235}U+^{238}U)/^{238}U$ in natural uranium which is equal to 1.0072;
   $N_A$: the Avogadro constant;
   $M(_{92}^{232}U)$: a molar mass of $^{238}U$;

$$T_{\frac{1}{2}}(_{92}^{238}U)$$

a half-life of $^{238}U$;
   ln: a natural logarithm;
   $M_{ech}$: a mass of the sample;
   $S_n(609 \text{ keV})$: the net area in the 609 keV line;
   $\text{Eff}_{609 \text{ keV}}$: an efficiency of the scintillator detector at 609 keV;
   $I_{609 \text{ keV}}(_{83}^{214}Bi)$: an emission intensity of $^{214}Bi$ at 609 keV;
   $T_C$: a counting "live time" corrected for a dead time of the scintillator detector.

8. The method according to claim 1, wherein the corrected mass concentration of uranium is calculated by multiplying the initial mass concentration of uranium and the corrective coefficient.

9. The method according to claim 1, wherein the corrective coefficient $K(d,h,Cm_{U0})$ is calculated using an equation of the following form:

$$K(d,h,Cm_{U0}) = a_0 + a_1 \times Cm_{U0} + a_2 \times d + a_3 \times h + a_4 \times d \times h + a_5 \times d \times h \times Cm_{U0} + a_6 \times Cm_{U0}^3 + a_7 h^3$$

where d is the parameter that is representative of the density, h the parameter that is representative of the height, $Cm_{U0}$ is the initial mass concentration of uranium, and $a_0$ to $a_7$ are coefficients.

10. A device for assessing a concentration of uranium in a sample of a uranium-bearing material, the sample having a density and a height, the device comprising:
   an acquisition module configured for acquiring an energy spectrum of gamma radiation of the sample by a detector, the energy spectrum comprising at least a first energy band between 87 keV and 110 keV, and a second energy band between 560 keV and 660 keV, the second energy band comprising a 609 keV energy line of $^{214}$Bi;
   a first calculation module configured for calculating an initial mass concentration of uranium by using an area of the first energy band, an area of the second energy band, and a net area of the 609 keV energy line of $^{214}$Bi;
   a measurement module configured for obtaining a measurement of a parameter that is representative of the height of the sample and a parameter that is representative of the density of the sample;
   a second calculation module configured for calculating a corrective coefficient, by using a parameter that is representative of the height of the sample, a parameter that is representative of the density of the sample, and the initial mass concentration of uranium calculated by the first calculation module; and a third calculation module configured for calculating a corrected mass concentration of uranium that is corrected by using the initial mass concentration of uranium and the corrective coefficient, each respectively calculated by the corresponding first calculation module and the second calculation module.

* * * * *